United States Patent [19]
Vosburgh

[11] 3,944,835
[45] Mar. 16, 1976

[54] HIGH ENERGY RADIATION DETECTOR HAVING IMPROVED REFLECTIVE BACKING FOR PHOSPHOR LAYER

[75] Inventor: Kirby G. Vosburgh, Schenectady, N.Y.

[73] Assignee: General Electric Company, Schenectady, N.Y.

[22] Filed: Sept. 25, 1974

[21] Appl. No.: 509,281

[52] U.S. Cl. .............. 250/487; 250/367; 250/368; 250/486
[51] Int. Cl.² .......................................... G01J 1/58
[58] Field of Search.... 250/361, 363, 358, 366–368, 250/458–460, 486–488, 320, 474, 482

[56] References Cited
UNITED STATES PATENTS

| | | | |
|---|---|---|---|
| 3,584,216 | 6/1971 | Tinney | 250/468 |
| 3,859,531 | 1/1975 | Van Dijk | 250/368 |

*Primary Examiner*—Harold A. Dixon
*Attorney, Agent, or Firm*—Jack E. Haken; Joseph T. Cohen; Jerome C. Squillaro

[57] ABSTRACT

A reflective backing member has an array of closely spaced corner reflectors adjacent to the input surface of a layer of material that absorbs high energy radiation events and converts them to light photons. The corner reflective surface causes rearward traveling light photons to be reflected along a path substantially parallel to the initial rearward path so that the reflective member provides a high quality reflective surface with less degradation of spatial resolution of an image produced by the light photons than occurs with conventional reflective backing members.

27 Claims, 14 Drawing Figures

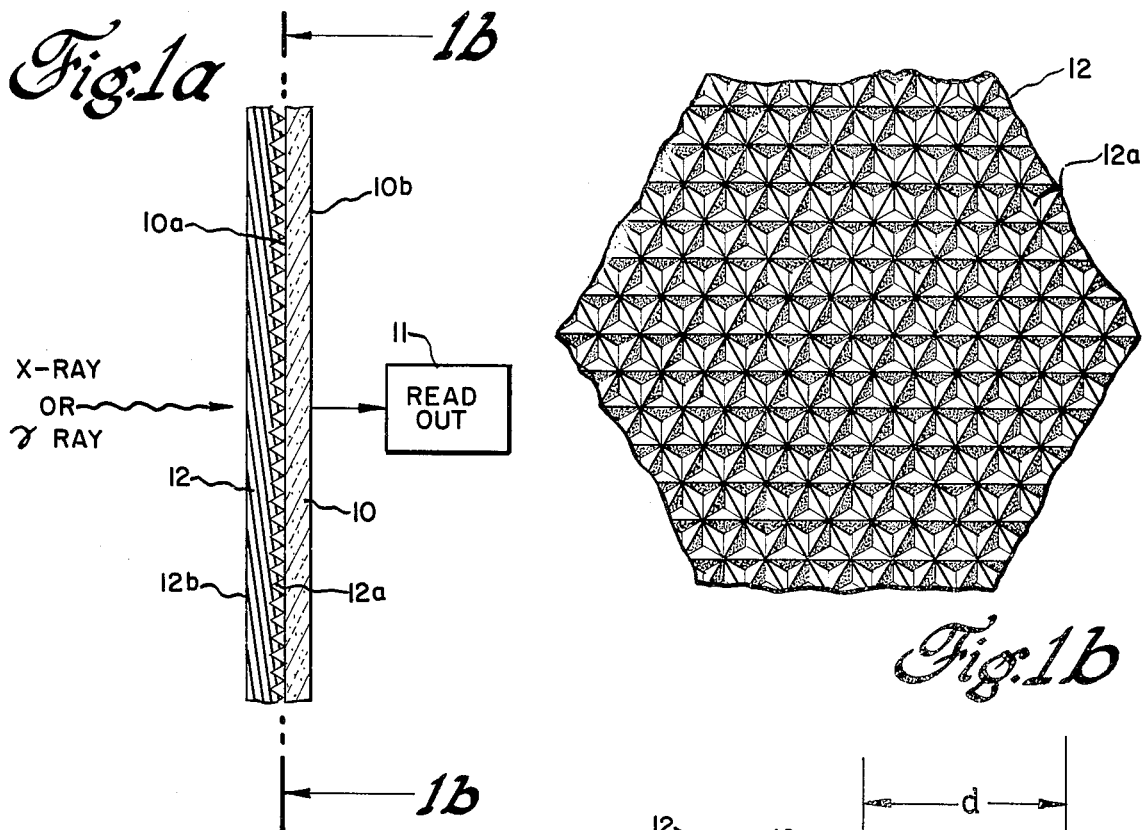
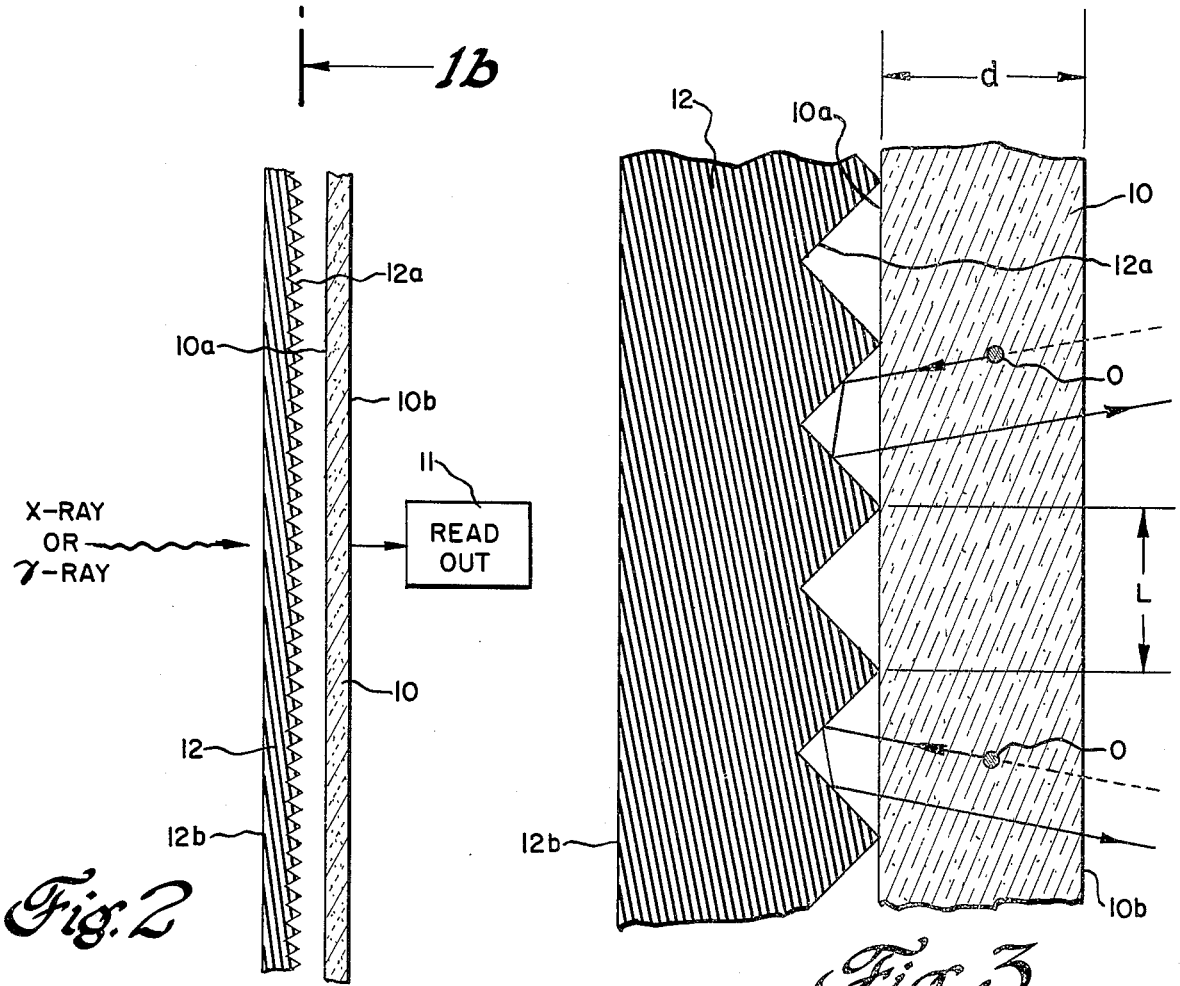

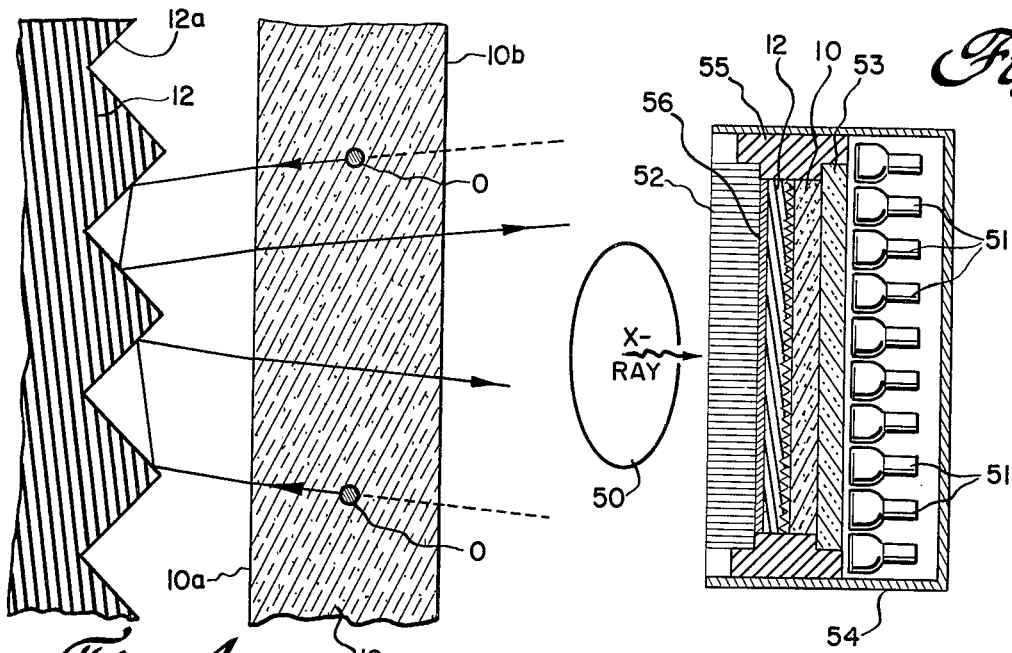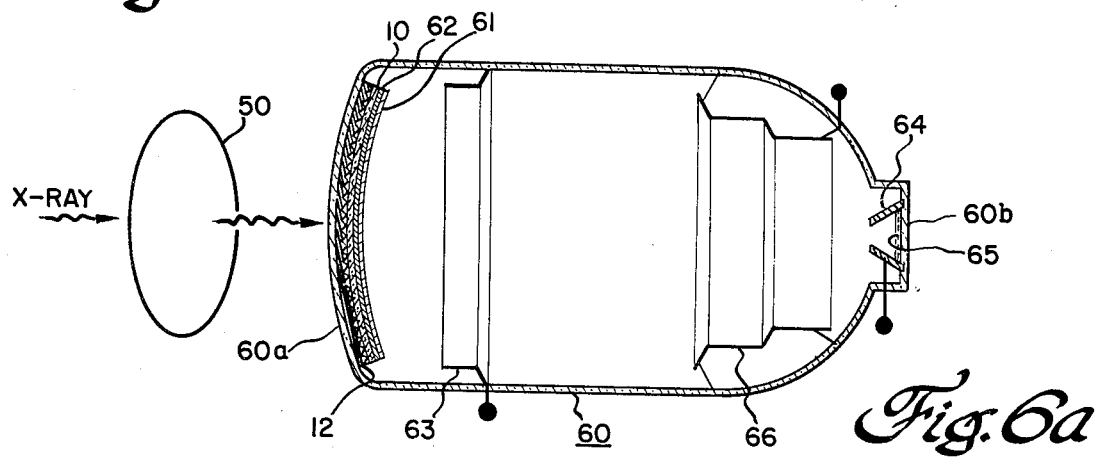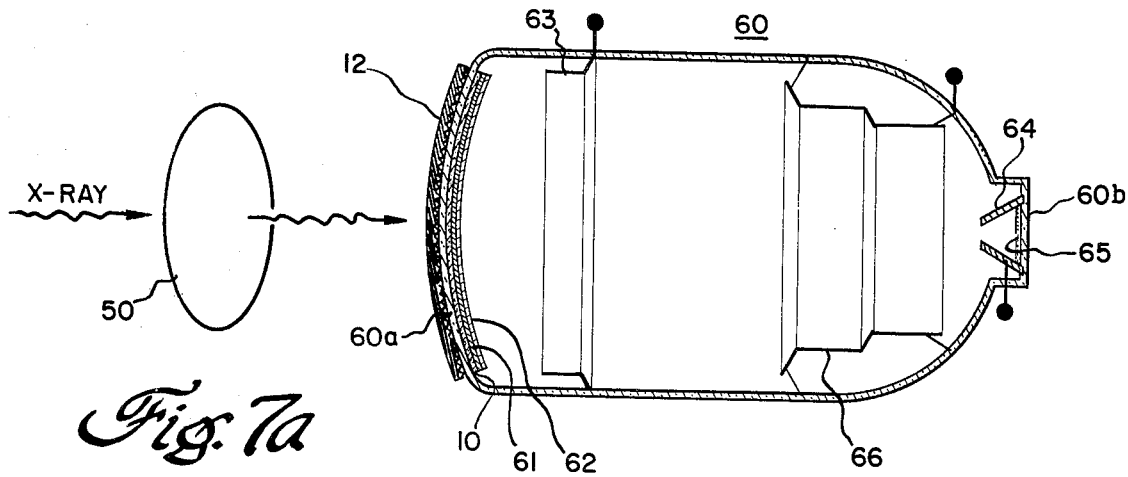

HIGH ENERGY RADIATION DETECTOR HAVING IMPROVED REFLECTIVE BACKING FOR PHOSPHOR LAYER

My invention relates to a reflective backing member for a phosphor layer or scintillator in high energy radiation detectors, and in particular, to a corner reflector type reflective surface for improving the spatial resolution of images developed by the detectors.

High energy radiation detectors have many applications, and are especially important in the medical field in apparatus such as the gamma camera and x-ray (or gamma ray) image intensifier. The high energy radiation referred to herein includes gamma rays, x-rays and high energy nuclear particles such as electrons, protons and neutrons. In the detector, the incident radiation quantum is absorbed in a phosphor material, and a portion of the resultant energy is converted to light photons which are emitted from the material and subsequently detected by a photosensitive system.

The gamma camera is utilized as a noninvasive diagnostic instrument for monitoring the distribution of a radio-emitting source by means of gamma ray detection and provides the physician with valuable diagnostic information. The gamma camera is used in nuclear medicine after a patient has been administered a small dose of a radiopharmaceutical, i.e., a short-lived gama-ray-emitting isotope (such as Technetium-99m), which has been formed onto an appropriate chemical compound so that the isotope either is attracted to, or avoids, a particular organ or region of the patient's body. The gamma camera is described in U.S. Pat. No. 3,011,057 to Anger. In the Anger patented camera, which is a gamma camera of the photomultiplier type, the incident gamma rays are absorbed in a single dense high atomic number phosphor crystal (the scintillator) and the resulting scintillations (events) are detected by an array of 19 phototubes, located adjacent to but spaced from the scintillator, whose outputs are processed to determine the incident gamma ray position and energy.

The x-ray image intensifier tube is especially useful for obtaining brighter x-ray images, particularly the images of body organs which generally are of low contrast. Conventional x-ray image intensifiers employ in the input end thereof a uniform layer of a dense high atomic number phosphor for absorbing the incident x-rays which have traversed the patient's body. The x-ray photon is absorbed in the phosphor layer, as is the gamma ray in the scintillator, and light photons are generated in the phosphor layer and emitted in all directions from the point of x-ray photon absorption. A thin photo-emitting coating deposited on the output surface of the phosphor layer emits photoelectrons in response to the incident light photons. The photoelectrons are then accelerated and electron-optically focussed onto a second phosphor screen at the output end of the image intensifier resulting in a brighter image than at the input phosphor screen.

The thickness of the scintillator crystal in conventional gamma cameras and the phosphor layer in conventional x-ray image intensifiers is invariably a compromise between a thick layer necessary for high gamma or x-ray absorption to obtain high sensitivity and attendant higher contrast of the displayed image, and a thin layer for good spatial resolution of the developed image. In addition, especially in the case of nuclear medicine wherein the number of gamma rays are limited and it is desired to discriminate among various initial photon energies, it is desirable to collect as many of the light photons as possible. Finally, the scintillator crystal and phosphor layer in the above-described conventional medical instruments are often provided with reflective or dispersive backing surfaces to increase the light output therefrom, but with a concomitant degradation of spatial resolution.

Therefore, one of the principal objects of my invention is to provide a reflective backing member for a layer of material responsive to high energy radiation events that yields light reflection comparable with conventional reflective backing members, but with less degradation of spatial resolution.

Another object of my invention is to provide a high quality reflective backing surface for a layer of phosphor material or scintillator crystal which will not substantially degrade the resolution of the reflection.

A further object of my invention is to provide an improved light reflector for a high energy radiation detector.

A still further object of my invention is to provide a light-reflective member which overcomes the conventional compromise between a desired thick dimension for a phosphor or scintillator crystal for high absorption and thin dimension for good spatial resolution.

Briefly stated, and in accordance with the objects of my invention, I provide an improved high energy radiation detector which basically consists of a conventional layer of material that is responsive to high energy radiation events such as x-ray or gamma rays and converts the absorbed high energy events to light photons, a read-out means for producing an optical display or electrical signals in response to the light photons and an improved reflective backing member for the layer of high energy radiation responsive material. The reflective backing member has a light-reflective surface defined by an array of closely spaced corner reflectors wherein the length of one side of the base of each reflector is less than the thickness of the high energy radiation responsive layer. The light-reflective backing member may be in contact with the input surface of the layer of high energy radiation responsive material, or may be slightly spaced therefrom without any degradation of resolution of the reflection.

The features of my invention which I desire to protect herein are pointed out with particularity in the appended claims. The invention itself, however, both as to its organization and method of operation, together with further objects and advantages thereof, may best be understood by reference to the following description taken in connection with the accompanying drawings wherein like parts in each of the several figures are identified by the same reference character, and wherein:

FIG. 1a is a partially schematic sectional side view of a first embodiment of my improved high energy radiation detector;

FIG. 1b is a view of the reflective surface of the reflective backing member component in FIG. 1a taken along line 1b—1b;

FIG. 2 is a partially schematic sectional side view of a second embodiment of my improved detector;

FIG. 3 is an enlarged fragmentary sectional view of the reflective backing member and phosphor layer portion of the detector depicted in FIG. 1a;

FIG. 4 is an enlarged fragmentary sectional view of the reflective backing member and phosphor layer depicted in FIG. 2;

FIG. 5 is a view, in partial section, of a scintillation type gamma camera application of my improved high energy radiation detector;

FIG. 6a is a sectional view of an x-ray image intensifier application of my improved high energy radiation detector;

FIG. 6b is an enlarged fragmentary sectional view of the input portion of the image intensifier depicted in FIG. 6a;

FIG. 7a is a sectional view of a second embodiment of an x-ray image intensifier application of my high energy radiation detector invention;

Figure 6B:
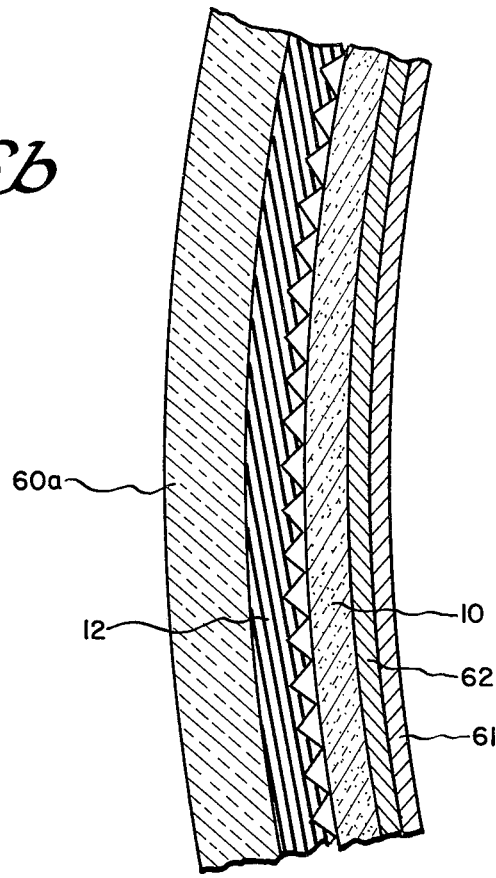

Referring now in particular to FIG. 1a, there is shown a simplified drawing of a first embodiment of my improved high energy radiation detector which basically consists of a uniform layer 10 of material responsive to high energy radiation events such as x-rays, gamma rays or particles and converts such events absorbed in the layer to light photons, the read-out means 11 for producing optical or electronic signals in response to the light photons emitted by layer 10, and a reflective backing member 12 for layer 10.

My invention is specifically directed to the form of the reflective surface on reflective backing member 12, that is, the surface 12a thereof closest to the near (input) major surface 10a of the high energy radiation responsive layer 10. The form of this reflective surface, in accordance with my invention, is an array of closely spaced corner reflectors indicated by the sawtooth surface 12a in FIG. 1a, and shown more clearly in FIG. 1b. The corner reflector may be geometrically defined as consisting of three planar sides forming identical isosceles triangles having a common vertex and an open base forming an equilateral triangle. Each side of the corner reflector is respectively perpendicular to the other two sides, and thus the angle of each of the three isosceles triangles at the common vertex is 90°. However, my invention is not limited to having such angle be only 90°, and the reflective backing member provides satisfactory service with the angle of each of the three isosceles triangles at the common vertex being in the range of 85° to 95°; nor do such angles necessarily have to be equal, or the isosceles triangles forming the three sides being identical, although in most cases the common vertex angles are equal and the triangles identical. The thickness of the body of material forming reflective backing member 12 is not critical, but should be sufficiently thin so that it does not absorb a significant fraction of the incident high energy radiation which passes through member 12 prior to being absorbed in layer 10. Although the body of reflective backing member 12 may, in some instances, be fabricated of the same material as the reflective surface 12a forming the corner reflectors, this is not usually the case and the body of member 12 is typically fabricated from glass, metal (of low atomic number, such as aluminum), or any rigid plastic whereas the reflective surface 12a of the array of corner reflectors is typically a thin coating of metal (such as aluminum), a lacquer, or metallic paint which typically is in the order of 100 Angstroms thickness and is applied to the corner reflective surface by any suitable means such as evaporation or spraying. Actually, there is no limitation on the thickness of the reflective coating.

The high energy radiation responsive layer 10 is formed of a phosphor material. In the case of an x-ray image intensifier application of my detector, layer 10 is thin (in the order of 3 to 10 mils thickness), and is typically formed by evaporating polycrystalline cesium iodide or forming granular silver-activated zinc cadmium sulfide or other phosphors in thin layer form on the inner surface of the image intensifier tube face plate. In the case of a gamma ray image intensifier or gamma ray camera application of my detector, layer 10 is thicker (in the order of 0.5 inch thickness) and is typically formed of a single crystal (called the scintillator in nuclear medicine terminology) of thallium-activated sodium iodide NaI (T$l$), CsI(T$l$) or CsI(Na). In either application, layer 10 is preferably of uniform thickness, but the input 10a major surface thereof may conform to the corner reflector irregularities of member 12 so that the phosphor material of layer 10 occupies the voids formed by the corner reflectors.

The read-out means 11 is typically a display device for recording optical or electrical signals representing the coordinate position and energy of the incident high energy radiation event absorbed in phosphor layer 10. The signals are generally displayed on an output phosphor screen, cathode ray tube, or may be recorded on magnetic type or other recording medium for storing the coordinate and energy information for later read-out on photographic film or a cathode ray tube.

As indicated in the side view of FIG. 1a, the high energy radiation input surface 12b of reflective backing member 12 may be planar (or curved in the same manner as would be the output surface 12a) so that such member is also of substantially uniform thickness, except for the variations along the corner reflective surface thereof. However, this generally uniform thickness is not a limitation since the material and, or, thickness thereof selected for the body of reflective backing member 12 is such that the incident high energy radiation is absorbed at most only to a slight degree therein, and the prime purpose of the body of member 12 is to provide mechanical support for the corner reflective surface.

A front view of the corner reflective surface 12a of member 12 is illustrated in FIG. 1b which clearly shows the three planar sides of each corner reflector and the common vertex of the three isosceles triangles formed thereby. The array of corner reflectors is typically a hexagonal array with the corner reflectors oriented in horizontal rows and columns oriented at 60° relative to the rows, and each corner reflector bordering the adjacent corner reflectors. The shape of reflective backing member 12 is determined primarily by convenience and is typically circular or square.

In FIG. 1a the reflective backing member 12 is illustrated as being in contact with the input major surface 10a of high energy radiation responsive layer 10. In FIG. 2, there is a pronounced spacing between these two members. As will be shown with reference to FIGS. 3 and 4, both embodiments of my high energy radiation detector have approximately the same operating characteristics and each has utility in specific applications. Thus, the contacting embodiment illustrated in FIG. 1a is utilized in most applications where reflective backing member 12 is located within a housing or glass envelope of the medical instrument in which my invention is especially valuable. However, in cases where it may be desired, or necessary, to locate reflective backing member outside the glass envelope, the spaced-apart embodiment of FIG. 2 finds merit.

As noted in FIG. 3, and also being true in all the FIGURES, the periodicity of the corner reflectors is less than the thickness of layer 10. This requirement for the successful operation of my invention is indicated by the periodicity dimension L (length of one side of the corner reflector base) being less than the layer 10 thickness dimension d in FIG. 3, and is also true in FIGS. 4 and 8a–d. The operation of my invention will now be described with specific reference to FIG. 3. Assume that a high energy radiation event such as an x-ray photon or gamma ray photon passes through reflective backing member 12 and is absorbed in the high energy radiation-responsive layer 10. The absorbed incident photon is converted in layer 10 to light photons, a single high radiation event generally being converted to a plurality of light photons which may travel in all directions from the absorbed point O. The useful light photons are those that pass through the second major surface 10b of layer 10 which is opposite the first (input) major surface 10a. This second major surface of layer 10 may be designated as the output surface since the light photons passing therethrough are detected in the read-out means 11 for developing a suitable output signal representing the detected high energy radiation event absorbed in layer 10. A major portion of the light photons developed in layer 10 which are not initially directed toward the output surface 10b are directed back toward the input surface 10a as illustrated by the arrowheads issuing from the point of origin O of the light photons in layer 10. In conventional high energy radiation detectors, these rearward traveling light photons are redirected in a forward direction by means of a planar reflective backing member, or dispersed by a suitable dispersing backing member, or absorbed by a suitable absorption backing member. In the case of the conventional planar reflective member, considerable degradation of image resolution occurs because the apparent size of the light photon source spreads out due to the reflection. It is evident from FIG. 3 that a light photon directed rearward at a large angle (relative to a center-line axis parallel to the major surface of layer 10) is reflected from the surfaces of the nearest corner reflectors and redirected (reflected) through layer 10 along a path either identical with, or parallel to, its rearward traveling path. In the extreme case wherein the light photon is directed rearward at a small angle such that it impinges on the reflective surface of a more remote corner reflector, the angle of the path of such rearward traveling light photon is substantially normal to the reflective surface and therefore it is reflected substantially along the same path back through layer 10. Reflective backing member 12 is thus seen to provide a high quality reflective surface which provides comparable light reflection, and hence comparable light output, as the conventional planar reflected surfaces, but with substantially less degradation of spatial resolution than occurs with such conventional reflective (or dispersive) surfaces. This feature is brought about by the fact that the right angle, or substantially right angle, surfaces of the corner reflectors cause the parallel (or coincident) reflected path of the light photons through layer 10.

Referring now to FIG. 4, it is evident that the same parallel (or coincident) orientation of the reflected light photons is obtained when reflective backing member 12 is spaced from high energy radiation responsive layer 10. The only difference between the operation of the embodiments illustrated in FIGS. 3 and 4 is that in FIG. 4 there is a longer path of travel of the light photon in the medium between the input surface 10a of layer 10 and the reflective surface 12a of the corner reflector. In the FIG. 3 embodiment, the effect of any difference in refraction indices between the material forming layer 10 and the vacuum, air or other material in the void formed by the reflective surfaces 12a of the corner reflectors has been neglected due to the short paths of travel within such latter region. However, in the FIG. 4 embodiment the length of travel in such void or other material is substantial and cannot realistically be neglected. However, as depicted in FIG. 4, any refraction of the light photon when passing through the layer 10 surface-void interface is compensated for by a complementary refraction in the return pass through the interface and thus the same parallel relationship occurs as in the FIG. 3 embodiment. Also, it should be evident that in both the FIGS. 3 and 4 embodiments, the alignment of the plane of the corner reflectors relative to the input surface 10a of layer 10 is not critical, that is, the plane of the corner reflectors is, in most instances, parallel to the input surface of layer 10 but a misalignment (i.e., nonparallelism) between such planes, or surface irregularity on input surface 10a of layer 10 have minimal effects on the path of the reflected light photons.

Referring now to FIG. 5, there is shown a nuclear medicine instrument conventionally described as a gamma camera for detecting gamma ray emission from a patient 50 after he has beeen administered a small dose of a radiopharmaceutical. In the gamma camera, an array of phototubes 51 is utilized as the light photon detector for converting the light photons emitted from the high energy radiation responsive layer (scintillator) 10 to electrical signals for further processing to determine the incident gamma ray position and energy. The gamma camera includes as components arranged in optical alignment a suitable collimator 52 which may typically be a parallel hole collimator fabricated of lead, reflective backing member 12, scintillator 10, a glass support plate 53 and finally the phototubes 51. Scintillator 10 is conventionally a single circular shaped crystal, as noted hereinabove, and is of planar configuration so that reflective backing member 12 is also a planar member (except for the corner reflector surfaces 12a thereon.)

Collimator 52 may be suitably fastened to the outside of the open input end of a light-tight housing 54, such as being bolted thereto. Housing 54 is generally a hollow cylindrical member fabricated of a suitable metal such as steel. Alternatively, housing 54 may be a glass envelope which is not evacuated in the gamma camera application. In such case, the glass envelope merely serves as a vapor barrier and can have a flat input end, and be of thinner dimension than the glass envelope for the x-ray image intensifier application, to be described hereinafter, which must maintain a vacuum therein. For this reason, (the thinness of the glass envelope) reflective backing member 12 can readily be located outside the glass envelope in such version of the gamma camera and be equivalent to the FIGS. 2 and 4 embodiments.

Scintillator 10 is disposed near the input end of housing 54, and is supported along its output surface by being sealed to a glass plate 53 that has its peripheral surface sealed to a flange 55 fastened at the open input end of housing 54. A suitable optical grease is often used for coupling the scintillator 10 to glass plate 35. Scintillator 10 is also sealed along its peripheral surface to flange 55. An aluminum (or other low atomic number material) window is conventionally employed in gamma cameras, interposed between collimator 52 and scintillator 10 for purposes of preventing extraneous light from entering housing 54. However, reflective backing member 12 is generally opaque so that it prevents the entrance of extraneous light to housing 54, and the aluminum window is therefore not required herein, but may be utilized as a mechanical support member 56 (of low gamma ray absorption) for the reflective backing member 12 by being sealed to the non-reflective surface thereof and therefore be interposed between collimator 52 and member 12. Reflective backing member 12, scintillator 10 and glass plate 53 are sealed within flange 55 by means of a suitable adhesive such as an epoxy resin. Reflective backing member 12 has the protruding edges of its reflective surface 12a preferably in contact with the input surface 10a of scintillator crystal 10 for providing mechanical support to the assembly. Member 12 may also be supported along its input surface 12b by the output end of collimator 52, or is fastened thereto for additional mechanical support of the assembly. The specific details of the various supports for components 51, 52 and 53 will not be described herein since they are conventional and do not directly relate to my invention.

Housing 54 typically has a diameter in the order of 18 inches for a typical 13 inch diameter scintillator 10 of approximately 0.5 inch thickness. Housing 54 is preferably backed with lead to provide shielding against extraneous gamma rays. The electrical connections to phototubes 51 are not shown herein for purposes of simplicity since my invention is directed to the input end of housing 54. The electrical signal outputs of the phototubes are supplied to the read-out means 11 which includes electronic circuitry for resolving the phototube output signals into signals representing the coordinate of position and energy of each of the pulses of light sensed by the phototubes. Readout means 11 further includes a suitable device for recording the coordinates of the detected scintillation.

A typical resolution for a gamma camera is approximately one line pair per centimeter. In the case of a gamma camera, it is essential to collect a large fraction of the light photons since the gamma ray energy is determined from a mathematical computation involving the total detected light intensity. Thus, the number of light photons detected must be high to alleviate statistical scatter in the energy determination. The advantage of my reflective backing member in providing a high quality reflective surface is therefore of great significance in gamma camera applications of my detector. The use of my reflective backing member also permits the use of a thicker scintillator, to approximately 0.75 inch, while maintaining the spatial and energy resolution of a 0.5 inch thick scintillator, thereby increasing the gamma ray absorption and thus increasing the gamma camera efficiency.

Referring now to FIG. 6a, there is shown an x-ray image intensifier tube of conventional design except for the use of my reflective backing member 12. The x-ray image intensifier tube is comprised of an evacuated glass envelope 60 generally circular in cross section and having a concave curved input end (face plate) 60a which conventionally has a uniform phosphor layer deposited on the inner surface thereof or on a thin aluminum dish within the glass envelope spaced slightly from the face plate. In accordance with my invention, however, reflective backing member 12 is interposed between face plate 60a and phosphor layer 10. Reflective backing member 12 is curved to conform to face plate 60a and may be directly supported on the face plate 60a, or may be spaced therefrom and supported from the side of housing 60 along its peripheral surface, as well as being supported along the input surface 10a of the phosphor layer. Alternatively, reflecting backing member 12 may have its input (nonreflective surface) supported on a thin metal (such as aluminum) or glass dish within the glass envelope spaced slightly from the face plate. Uniform phosphor layer 10 is of thickness in the range of 3 to 10 mils in conventional x-ray image intensifiers, but can have an increased thickness up to approximately 15 mils when using my reflective backing member without an increase in degradation of spatial resolution. The phosphor layer, formed of materials described hereinabove, has deposited on its output surface 10b a thin film 61 of photoemitter material of thickness of approximately 100 Angstroms. Photoemitter film 61 may be directly deposited on the phosphor layer, or alternatively and more generally, it is deposited on an intermediate thin film 62 which isolates the alkali metal of the photoemitter material from the phosphor. The photoemitter material is selected to match the particular phosphor employed and may be of the common types known as S-20 (a compound of antimony, cesium, sodium and potassium) or S-11 (a compound of cesium, antimony and oxygen). Isolating layer 62 may be silicone resin as a typical example.

Face plate 60a, as well as phosphor layer 10, films 61, 62 and reflective backing member 12 are curved concave to improve the electron-optical focussing of the photoelectrons emitted by photoemitter film 61 in response to the light photons transmitted from phosphor layer 10 to photoemitter film 61. For each x-ray photon absorbed in phosphor layer 10, there are generated in the order of 1,000 light photons. FIG. 6b illustrates this input end of the x-ray image intensifier tube in greater detail. The photoelectrons emitted by photoemitter film 61 are focussed by an electrode 63 maintained at a potential of several hundred volts d.c. positive with respect to ground and are accelerated to approximately 25 kilovolts by means of electrode 64 positioned within envelope 60 in close proximity to output phosphor screen 65, and beyond the crossover point of the electron paths at the output end of the image intensifier tube. The electrodes 63, 64 (and 66) are suitably shaped to provide electron-optical focussing of the accelerated photoelectrons onto the second uniform phosphor screen, layer 65, deposited on the inner surface of the glass envelope 60 at the output end 60b thereof. The image appearing on output phosphor screen 65 is a brighter version of the image on the input phosphor screen (phosphor layer 10) and can be viewed directly by the physician or be subjected to further processing. An additional electrode 66 may be provided within envelope 60 and positioned between electrodes 63 and 64, and operated at a potential intermediate the potentials of electrodes 62 and 64, and functions to provide variable magnification imaging to thereby permit the imaging on output phosphor layer 65 of only a selected portion of the image appearing on input phosphor layer 10.

The use of my reflective backing member 12 avoids the conventional compromise between the use of a thick and thin phosphor layer 10 since it reduces degradation of spatial resolution as compared to the conventional reflective backing surfaces. Thus, the ability to utilize thicker phosphor layers 10 permits higher x-ray absorption, and resultant higher sensitivity and with less loss in spatial resoltuion and local contrast than occurs in conventional image intensifiers, or alternatively, permits the use of conventional thickness phosphor layers 10 with increased spatial resolution as compared to conventional image intensifiers. A 7 mil thick phosphor layer in a conventional x-ray image intensifier yields a resolution of 3 to 4 line pairs per millimeter. A resolution of approximately 5 to 6 line pairs per millimeter is obtainable with my invention when using a 7 mil thick phosphor layer. The thickness of the phosphor layer in conventional image intensifiers of 3 to 10 mils yields a relatively low x-ray absorption in the order of 15 to 40 percent of the incident rays. By being able to increase this phosphor layer thickness to 5 to 15 mils due to my invention, without concomittant decrease in spatial resolution, the x-ray absorption can be increased to approximately 25 to 55 percent.

A second embodiment of an x-ray image intensifier utilizing my reflective backing member is depicted in FIG. 7a which differs from the FIG. 6a embodiment in that member 12 is suitably supported along the outer surface of face plate 60a instead of being supported along the inner surface (or supported within glass envelope 60 and spaced from the face plate). Phosphor layer 10 is formed along the inner surface of face plate 60a, and thus this embodiment of my member 12-phosphor 10 interface corresponds to the spacedapart embodiment of FIGS. 2 and 4. In all other respects the FIGS. 7a and 6a embodiments are the same.

Figure 7B:
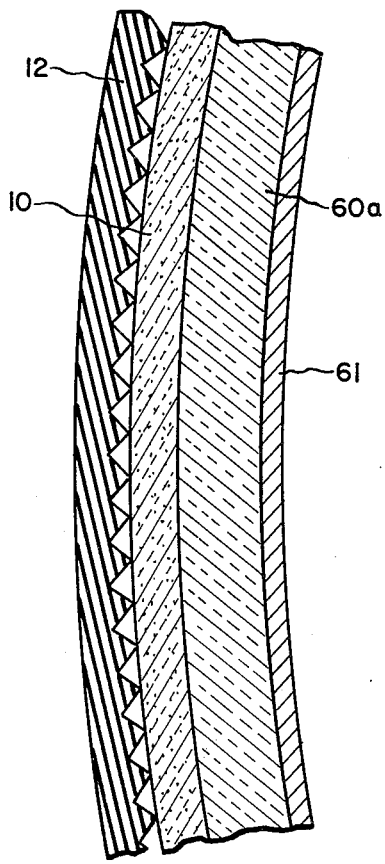
FIG. 7b is an enlarged fragmentary sectional view of the input portion of a gamma ray image intensifier application of my high energy radiation detector invention.

The image intensifier tube described with reference to FIGS. 6a and 7a can also be utilized in nuclear medicine as a gamma ray image intensifier with the following changes. Phosphor layer 10 is formed of a single curved scintillator crystal having a uniform thickness in the order of one-half inch (or more), and is formed of the materials described hereinabove for the gamma camera. Scintillator 10 is preferably deposited along the outer (convex) surface of face plate 60a of evacuated glass envelope 60 as shown in FIG. 7b. In such case, reflective backing member 12 is suitably sealed to scintillator 10, such as by having a filler material in the voids defined by the corner reflector surfaces 12a, be sealed to the input surface 10a of the scintillator. Member 12 may also be sealed along its peripheral surface to a flange (not shown) at the tube input end to provide a means for isolating the scintillator 10 from the ambient. Any sealed spacing between scintillator or phosphor layer 10 and reflective backing member 12 in any of these embodiments may be back-filled with an atmosphere of dry nitrogen, if desired. Photoemitter film 61 is of uniform thickness, again of approximately 100 Angstrom, and is formed of a material selected to match the particular scintillator crystal employed and having high quantum efficiency at the wavelength of scintillation of scintillator 10, typical photoemitter film material being a mixture of potassium, cesium and antimony. Isolating film 62 is not required in this embodiment since the glass face plate 60a chemically isolates scintillator 10 from photoemitter film 61. Approximately 500 photoelectrons are emitted from photoemitter film 61 for each 140 keV energy gamma ray absorbed in scintillator 10. A suitable gamma radiation collimator, such as described with reference to FIG. 5, (typically a one-inch thick lead sheet with a large number of small equal size, equally spaced holes therethrough) is generally utilized and interposed between reflective backing member 12 and the particular organ or other region of the body of a patient 50 being imaged. the collimator is generally a planar type member as illustrated in FIG. 5 and need not conform to the concave shape of face plate 60a in the gamma ray image intensifier. Alternatively, the recently developed coded imaging aperture system may be utilized instead of a gamma ray collimator.

In the x-ray image intensifier tube, the phosphor layer is much thinner than in the case of a gamma ray image intensifier and for that reason the smaller thickness layer is often evaporated on the inner surface of the face plate for the x-ray application. The substantially thicker scintillator in the gamma ray application is not conductive to evaporation techniques and therefore is generally formed along the outer surface of the face plate 60a. Alteratively, scintillator 10 may be placed on the inner (concave) surface of face plate 60a, however, this is not the preferred arrangement since additional isolating means (film 62) may then be required between the scintillator and photoemitter film 61 as in the case of the x-ray image intensifier, and this is difficult to accomplish at a one-half inch thickness of the scintillator.

Figure 8A:
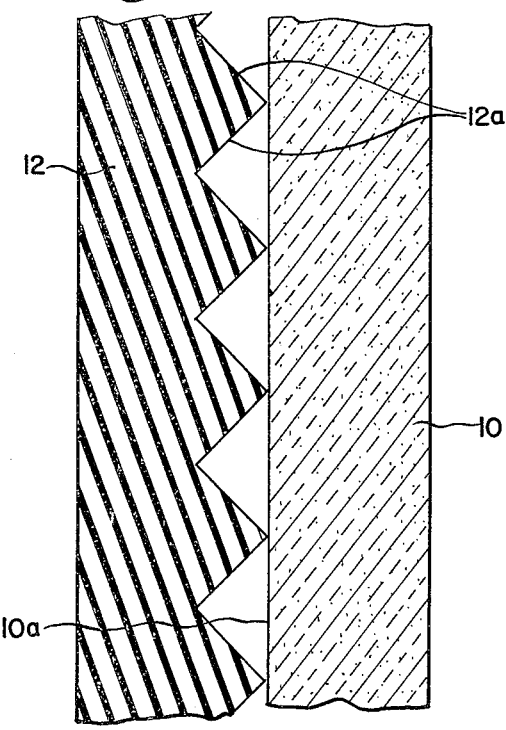
FIG. 8a is an enlarged fragmentary sectional view of a first embodiment of the reflective backing member and phosphor layer portion of my improved detector.
Figure 8B:
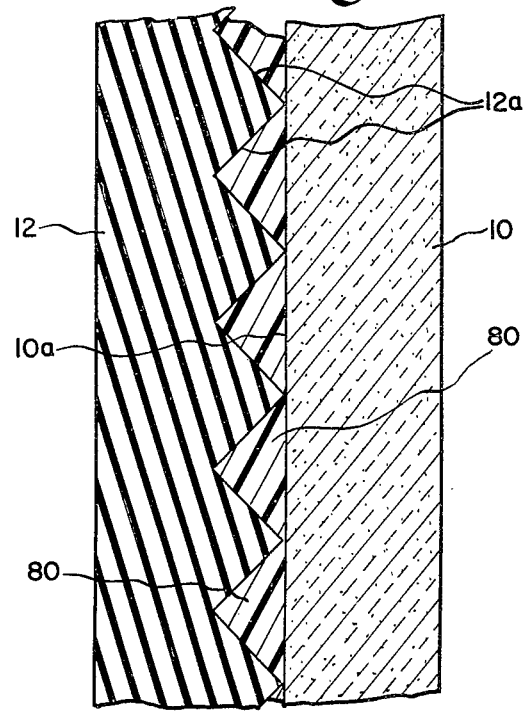
FIG. 8b is an enlarged fragmentary sectional view of a second embodiment of the reflective backing member and phosphor layer.
Figure 8C:
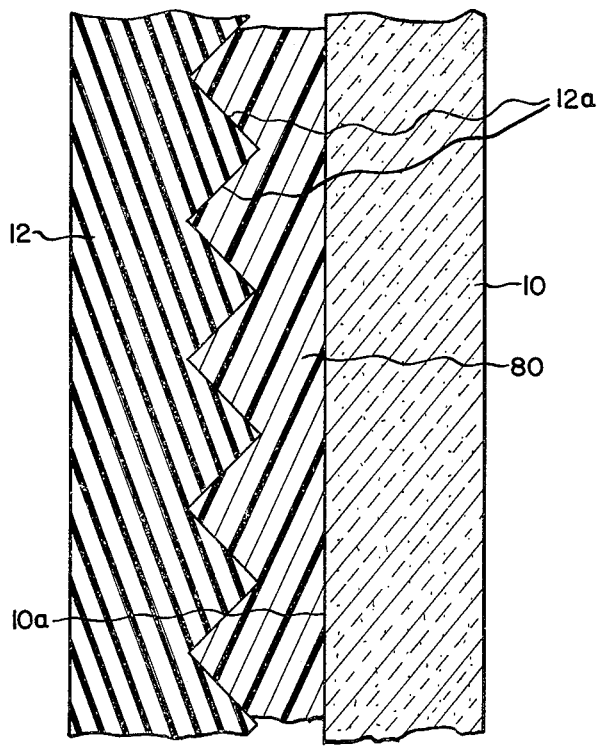
FIG. 8c is an enlarged fragmentary sectional view of a third embodiment of the reflective backing member and phosphor layer.
Figure 8D:
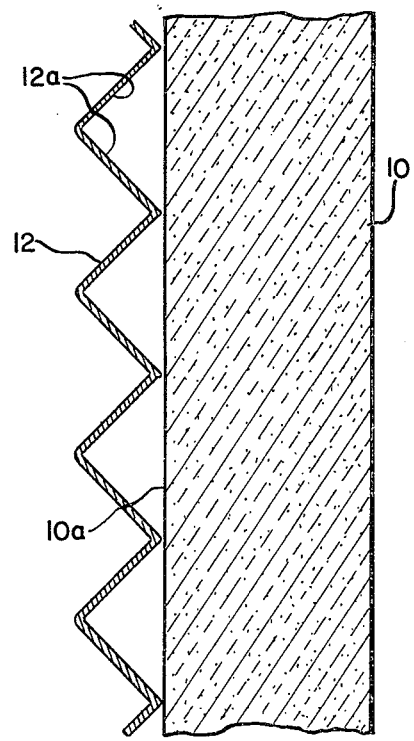
FIG. 8d is an enlarged fragmentary sectional view of a fourth embodiment of the reflective backing member and phosphor layer.

Referring now to FIG. 8a, there is shown an enlarged fragmentary view of a first embodiment of reflective backing member 12 and high energy radiation responsive layer 10 wherein the projecting ends of the corner reflector surfaces 12a are in contact with the input surface 10a of layer 10. In this first embodiment, the void between the corner reflector surfaces 12a and the input surface 10a of layer 10 remains as such and thus constitutes a vacuum or ambient air, depending upon the application of the detector. In FIG. 8b, the void is filled with a suitable light-transparent material 80 such as transparent plastic or optical coupling grease for purposes of adding structural rigidity to the assembly of reflective backing member 12 and high energy radiation responsive layer 10. Further, material 80 can be selected, as in the case of optical grease, to provide a more closely matched index of refraction to the material constituting layer 10 so that the rearward traveling light photons suffer less refraction in their paths of travel. FIG. 8c illustrates a third embodiment of the reflective backing member 12 and layer 10 with a spacing therebetween, as in FIG. 2, and having such spacing occupied by the same material 80 as indicated with respect to the FIG. 8b embodiment. Due to the spaced apart nature of elements 10 and 12 in FIG. 8c, the function of material 80 in adding mechanical support to this assembly is even more important in this embodiment. FIG. 8d is a fourth embodiment of the reflective backing member 12 in which the backing member is substantially different from the three embodiments illustrated in FIGS. 8a–c. In particular, instead of utilizing a body of material in the nonreflective portion of member 12, the fourth embodiment is fabricated of the light-reflective material in thin form. Thus, reflective backing member 12 in the FIG. 8d embodiment may be a sheet of metal (such as aluminum) or plastic (that is subsequently coated wiht a light-reflective material on surface 12a) that has been stamped to provide the desired geometric shape of the corner reflectors in the sheet. The sheet preferably has sufficient thickness in the order of 15 mils so that it remains rigid and can be supported along its peripheral surface to remain in contact with the input surface 10a of layer 10. As in the case of the FIG. 8b embodiment, suitable filler material can be provided in the voids between the corner reflector array shaped sheet 12 and input surface 10a of layer 10 for adding mechanical support to the assembly thereof, and may provide better matching of the refraction indices, as noted above.

The microstructure of the array of corner reflectors can be fabricated in any of a number of conventional methods. One method is to cast the structure in a pliable material, such as plastic moulding compound and then to deposit a reflective film such as aluminum upon the cast structure. Other methods for forming the structure are by using a pressing method or by molding. As noted hereinabove, the periodicity of the microstructure is less than the thickness of layer 10. In the nuclear medicine application, i.e., the gamma camera, or gamma ray image intensifier, the periodicity (L dimension in FIG. 3) is approximately 100 mils. In the fluoroscopy application (i.e., x-ray image intensifier) the periodicity is approximately 1 mil.

From the foregoing description, it can be appreciated that may invention makes available an improved high energy radiation detector which is especially suitable for use in imaging devices such as a gamma camera or x-ray or gamma ray image intensifier tube for obtaining increased light output from the phosphor layer without the attendant increased degradation of spatial resolution that occurs in conventional imaging devices. As a result of my invention, I overcome the conventional compromise between a desired thick dimension for a phosphor layer for obtaining high absorption, and the thin dimension required for good spatial resolution.

Having described a number of specific embodiments of my improved high energy radiation detector, it is believed obvious that modification and variation of my invention is possible in light of the above teachings. Thus, the body of the reflective backing member may be fabricated from any of a number of materials which are substantially transparent (low atomic number material) to the high energy radiation, or of a more absorbing material but having much thinner dimensions so that the absorption of the high energy radiation is low. Also, the phosphor layer or scintillator can be deposited on surface 12a of reflective backing member 12 so as to fill the voids therein in cases wherein this nonuniformity of layer 10 can be tolerated. It is, therefore, to be understood that changes may be made in the particular embodiments of my invention as described which are within the full intended scope of the invention as defined by the following claims.

What I claim as new and desire to secure by Letters Patent of the United States is:

1. An improved high energy radiation detector comprising
   a layer of material responsive to high energy radiation events originating external of the detector for converting the high energy radiation events absorbed in the layer of material to light photons, and
   read-out means in communication with said layer of high energy radiation responsive material for producing signals in response to the light photons emitted by said layer,
   the improvement consisting of
   a member positioned adjacent said layer of high energy radiation responsive material along a first major surface thereof nearest the source of high energy radiation events, said member having a light-reflective first major surface positioned along the first major surface of said layer of high energy radiation responsive material and being defined by a plurality of closely spaced corner reflectors wherein each corner reflector consists of three sides forming substantially identical isosceles triangles having a common vertex and an open base forming an equilateral triangle, the length of one side of the base being less than the thickness of the layer of high energy radiation responsive material, the corner reflectors reflecting rearward traveling light photons in said layer wherein each reflected path is substantially parallel to the incident path of the rearward traveling light photon so that said reflective member provides a high quality reflective surface.

2. The improved detector set forth in claim 1 wherein the angle of each of the three isosceles triangles at the common vertex is in the range of 85° to 95°.

3. The improved detector set forth in claim 1 wherein the angle of each of the three isosceles triangles at the common vertex is substantially 90°.

4. The improved detector set forth in claim 1 wherein the first major surface of said layer of high energy radiation responsive material is in contact with protruding edges of the corner reflector surface of said reflective member.

5. The improved detector set forth in claim 1 wherein the layer of high energy radiation responsive material is of uniform thickness.

6. The improved detector set forth in claim 1 wherein the three sides forming each corner reflector are each a planar surface.

7. The improved detector set forth in claim 1 and further comprising
   light-transparent means occupying the void defined by the three sides of each corner reflector and the first major surface of said layer of high energy radiation responsive material to provide mechanical support to the assembly of said layer of high energy radiation responsive material and reflective member.

8. The improved detector set forth in claim 1 wherein the first major surface of said layer of high energy radiation responsive material is slightly spaced from the corner reflective surface of said reflective member.

9. The improved detector set forth in claim 8 and further comprising
   light-transparent means occupying the void defined by the three sides of each corner reflector and the first major surface of said spaced apart layer of high energy radiation responsive material, said light-transparent means formed of a material having an index of refraction similar to the index of refraction of the material forming the layer of high energy radiation responsive material.

10. The improved detector set forth in claim 1 wherein
said reflective member is formed of a body of material substantially transparent to the high energy radiation events and the first major surface thereof is a thin film of highly light-reflective material deposited on the corner reflector surfaces of the body of high energy radiation transparent material.

11. The improved detector set forth in claim 10 wherein
the body of high energy radiation transparent material is formed of a low atomic number metal.

12. The improved detector set forth in claim 10 wherein
the thin film of highly light-reflective material is a thin film of metal.

13. The improved detector set forth in claim 1 wherein
said reflective member is a sheet of light-reflective material formed in the geometric shape of the corner reflectors.

14. The improved detector set forth in claim 13 wherein said reflective member is formed from a sheet of metal.

15. The improved detector set forth in claim 1 wherein
said layer of high energy radiation responsive material is a first phosphor layer for absorbing x-rays, said reflective member resulting in less degradation of spatial resolution of an image produced in the read-out means than occurs with conventional reflective backing members due to the parallel reflected light-photon paths, said reflective member overcoming the conventional compromise between a thick phosphor layer for high x-ray absorption and thin phosphor layer for good spatial resolution.

16. The improved detector set forth in claim 15 wherein
said read-out means is a second phosphor layer formed along an output end of an evacuated glass envelope,
said first phosphor layer formed along an input end of the evacuated glass envelope, a thin film of photo-emitter material deposited along a second major surface of said first layer of phosphor material on the side opposite the first major surface thereof, at least said first phosphor layer and the thin film of photoemitter material being disposed within the evacuated glass envelope so that the improved detector forms and x-ray image intensifier.

17. The x-ray image intensifier set forth in claim 16 wherein
the plurality of closely spaced corner reflectors are formed in a hexagonal array.

18. The x-ray image intensifier set forth in claim 16 wherein
the periodicity of the corner reflectors is approximately 1 mil.

19. The x-ray image intensifier set forth in claim 16 wherein
said reflective member is disposed within the evacuated glass envelope and is interposed between the input end thereof and said first phosphor layer.

20. The x-ray image intensifier set forth in claim 16 wherein
said reflective member is disposed external of the evacuated glass envelope and the light-reflective surface thereof is supported from the input end of the evacuated glass envelope.

21. The improved detector set forth in claim 1 wherein
said layer of high energy radiation responsive material is a single scintillator crystal for absorbing gamma rays, said reflective member resulting in less degradation of spatial resolution of an image produced in the read-out means than occurs with conventional reflective backing members due to the parallel reflective light photon-paths, said reflective member overcoming the conventional compromise between a thick scintillator crystal for high gamma ray absorption and thin scintillator crystal for good spatial resolution.

22. The improved detector set forth in claim 21 wherein
said read-out means is an array of phototubes spaced slightly from a second major surface of said scintillator crystal on the side opposite the first major surface thereof,
said scintillator crystal positioned along an input end of a housing containing said array of phototubes, and further comprising
a collimator for gamma radiation disposed along a second major surface of said reflective member on the side opposite the first major surface thereof so that the improved detector forms a gamma ray detector commonly known as the gamma camera.

23. The gamma camera set forth in claim 22 wherein the plurality of closely spaced corner reflectors are formed in a hexagonal array.

24. The gamma camera set forth in claim 22 wherein the periodicity of the corner reflectors is approximately 100 mils.

25. The improved detector set forth in claim 21 wherein
said read-out means is a phosphor layer formed along an output end of an evacuated glass envelope,
said scintillator crystal disposed along an input end of the evacuated glass envelope, a thin film of photo-emitter material deposited along a second major surface of said scintillator crystal on the side opposite the first major surface thereof and being disposed within the evacuated glass envelope,
and further comprising,
a collimator for gamma radiation disposed along a second major surface of said reflective member on the side opposite the first major surface thereof so that the improved detector forms a gamma ray image intensifier.

26. The gamma ray image intensifier set forth in claim 25 wherein
the periodicity of the corner reflectors is approximately 100 mils.

27. The gamma ray image intensifier set forth in claim 25 wherein
said reflective member is disposed external of the evacuated glass envelope with the light-reflective surface thereof facing the input end of the evacuated glass envelope, and said scintillator crystal is also disposed external of the evacuated glass envelope and is interposed between said reflective member and the input end of the evacuated glass envelope.

* * * * *